(12) United States Patent
Herrig et al.

(10) Patent No.: US 8,079,973 B2
(45) Date of Patent: Dec. 20, 2011

(54) VASCULAR ACCESS SYSTEM

(75) Inventors: Judson A. Herrig, Elko, MN (US);
Darren Braml, Bloomington, MN (US)

(73) Assignee: Hemosphere Inc., Eden Prairie, MN (US)

( * ) Notice: Subject to any disclaimer, the term of this patent is extended or adjusted under 35 U.S.C. 154(b) by 326 days.

(21) Appl. No.: 12/397,275

(22) Filed: Mar. 3, 2009

(65) Prior Publication Data

US 2009/0227932 A1    Sep. 10, 2009

Related U.S. Application Data

(60) Provisional application No. 61/034,125, filed on Mar. 5, 2008.

(51) Int. Cl.
*A61M 5/00* (2006.01)
*A61M 13/00* (2006.01)

(52) U.S. Cl. ............ 604/8; 604/6.16; 604/508

(58) Field of Classification Search ........... 604/6.16, 604/8, 9, 507, 508, 533
See application file for complete search history.

(56) References Cited

U.S. PATENT DOCUMENTS

| | | |
|---|---|---|
| 3,363,926 A | 1/1968 | Wilson |
| 3,490,438 A | 1/1970 | Stupka et al. |
| 3,683,926 A | 8/1972 | Suzuki |
| 3,814,137 A | 6/1974 | Martinez |
| 3,818,511 A | 6/1974 | Goldberg et al. |
| 3,826,257 A | 7/1974 | Buselmeier |
| 3,882,862 A | 5/1975 | Berend |
| 3,998,222 A | 12/1976 | Shihata |
| 4,076,023 A | 2/1978 | Martinez |
| 4,133,312 A | 1/1979 | Burd |
| 4,184,489 A | 1/1980 | Burd |
| 4,214,586 A | 7/1980 | Mericle |
| 4,318,401 A | 3/1982 | Zimmerman |
| 4,441,215 A * | 4/1984 | Kaster .............. 623/1.53 |
| 4,447,237 A | 5/1984 | Frisch et al. |
| 4,496,349 A | 1/1985 | Cosentino |
| 4,496,350 A | 1/1985 | Cosentino |
| 4,503,568 A * | 3/1985 | Madras ............. 623/1.3 |
| 4,550,447 A | 11/1985 | Seiler, Jr. |
| 4,619,641 A | 10/1986 | Schanzer |
| 4,734,094 A | 3/1988 | Jacob et al. |
| 4,753,236 A | 6/1988 | Healy |
| 4,771,777 A | 9/1988 | Horzewski et al. |
| 4,772,268 A | 9/1988 | Bates |
| 4,786,345 A | 11/1988 | Wood |

(Continued)

FOREIGN PATENT DOCUMENTS

DE    4418910    12/1995

(Continued)

OTHER PUBLICATIONS

International Search Report and Written Opinion for PCT Application No. PCT/US2009/035923 dated Jun. 3, 2009 in 11 pages.

(Continued)

*Primary Examiner* — Leslie Deak
(74) *Attorney, Agent, or Firm* — Knobbe Martens Olson & Bear LLP

(57) ABSTRACT

A connector system includes an engagement mechanism is provided that includes an engagement feature and a braided reinforcement coupled with a proximal portion of a catheter. The engagement feature can include one, two, or two or more barbs.

31 Claims, 8 Drawing Sheets

U.S. PATENT DOCUMENTS

| | | | |
|---|---|---|---|
| 4,790,826 A | 12/1988 | Elftman | |
| 4,822,341 A | 4/1989 | Colone | |
| 4,848,343 A | 7/1989 | Wallsten et al. | |
| 4,850,999 A * | 7/1989 | Planck | 623/1.44 |
| 4,856,938 A | 8/1989 | Kuehn | |
| 4,877,661 A | 10/1989 | House et al. | |
| 4,898,669 A | 2/1990 | Tesio | |
| 4,917,067 A | 4/1990 | Yoshida | |
| 4,917,087 A | 4/1990 | Walsh et al. | |
| 4,929,236 A | 5/1990 | Sampson | |
| 4,955,899 A | 9/1990 | Della Corna et al. | |
| 5,026,513 A | 6/1991 | House et al. | |
| 5,041,098 A | 8/1991 | Loiterman et al. | |
| 5,053,023 A | 10/1991 | Martin | |
| 5,061,275 A | 10/1991 | Wallsten et al. | |
| 5,061,276 A | 10/1991 | Tu et al. | |
| 5,064,435 A | 11/1991 | Porter | |
| 5,104,402 A | 4/1992 | Melbin | |
| 5,171,227 A | 12/1992 | Twardowski et al. | |
| 5,171,305 A | 12/1992 | Schickling et al. | |
| 5,192,289 A | 3/1993 | Jessen | |
| 5,192,310 A | 3/1993 | Herweck et al. | |
| 5,197,976 A | 3/1993 | Herweck et al. | |
| 5,330,500 A | 7/1994 | Song | |
| 5,399,168 A | 3/1995 | Wadsworth et al. | |
| 5,405,339 A * | 4/1995 | Kohnen et al. | 604/535 |
| 5,454,790 A | 10/1995 | Dubrul | |
| 5,476,451 A | 12/1995 | Ensminger et al. | |
| 5,496,294 A | 3/1996 | Hergenrother et al. | |
| 5,509,897 A | 4/1996 | Twardowski et al. | |
| 5,558,641 A | 9/1996 | Glantz | |
| 5,562,617 A | 10/1996 | Finch, Jr. et al. | |
| 5,562,618 A | 10/1996 | Cai et al. | |
| 5,607,463 A | 3/1997 | Schwartz et al. | |
| 5,637,088 A | 6/1997 | Wenner et al. | |
| 5,637,102 A | 6/1997 | Tolkoff et al. | |
| 5,647,855 A | 7/1997 | Trooskin | |
| 5,669,881 A | 9/1997 | Dunshee | |
| 5,674,272 A | 10/1997 | Bush et al. | |
| 5,676,346 A | 10/1997 | Leinsing | |
| 5,743,894 A | 4/1998 | Swisher | |
| 5,755,773 A | 5/1998 | Evans et al. | |
| 5,755,775 A | 5/1998 | Trerotola et al. | |
| 5,792,104 A | 8/1998 | Speckman et al. | |
| 5,797,879 A | 8/1998 | DeCampli | |
| 5,800,514 A * | 9/1998 | Nunez et al. | 623/1.51 |
| 5,800,522 A | 9/1998 | Campbell et al. | |
| 5,810,870 A | 9/1998 | Myers et al. | |
| 5,829,487 A | 11/1998 | Thomas et al. | |
| 5,830,224 A | 11/1998 | Cohn et al. | |
| 5,840,240 A | 11/1998 | Stenoien et al. | |
| 5,866,217 A | 2/1999 | Stenoien et al. | |
| 5,904,967 A | 5/1999 | Ezaki et al. | |
| 5,931,829 A | 8/1999 | Burbank et al. | |
| 5,931,865 A | 8/1999 | Silverman et al. | |
| 5,957,974 A | 9/1999 | Thompson et al. | |
| 5,997,562 A | 12/1999 | Zadno-Azizi | |
| 6,001,125 A | 12/1999 | Golds et al. | |
| 6,019,788 A | 2/2000 | Butters et al. | |
| 6,102,884 A | 8/2000 | Squitieri | |
| 6,156,016 A | 12/2000 | Maginot | |
| 6,231,085 B1 | 5/2001 | Olson | |
| 6,255,396 B1 | 7/2001 | Ding et al. | |
| 6,261,255 B1 | 7/2001 | Mullis et al. | |
| 6,261,257 B1 | 7/2001 | Uflacker et al. | |
| 6,319,279 B1 | 11/2001 | Shannon et al. | |
| 6,338,724 B1 | 1/2002 | Dossa | |
| 6,398,764 B1 | 6/2002 | Finch, Jr. et al. | |
| 6,402,767 B1 | 6/2002 | Nash et al. | |
| 6,436,132 B1 | 8/2002 | Patel et al. | |
| 6,582,409 B1 | 6/2003 | Squitieri | |
| 6,585,762 B1 | 7/2003 | Stanish | |
| 6,689,096 B1 | 2/2004 | Loubens et al. | |
| 6,689,157 B2 | 2/2004 | Madrid et al. | |
| 6,692,461 B2 | 2/2004 | Wantink | |
| 6,699,233 B2 | 3/2004 | Slanda et al. | |
| 6,702,748 B1 | 3/2004 | Nita et al. | |
| 6,702,781 B1 | 3/2004 | Reifart et al. | |
| 6,719,781 B1 | 4/2004 | Kim | |
| 6,719,783 B2 | 4/2004 | Lentz et al. | |
| 6,730,096 B2 | 5/2004 | Basta | |
| 6,733,459 B1 | 5/2004 | Atsumi | |
| 6,740,273 B2 | 5/2004 | Lee | |
| 6,749,574 B2 | 6/2004 | O'Keefe | |
| 6,752,826 B2 | 6/2004 | Holloway et al. | |
| 6,758,836 B2 | 7/2004 | Zawacki | |
| 6,926,735 B2 | 8/2005 | Henderson | |
| 6,976,952 B1 | 12/2005 | Maini et al. | |
| 7,011,645 B2 | 3/2006 | McGuckin, Jr. et al. | |
| 7,025,741 B2 | 4/2006 | Cull | |
| 7,101,356 B2 | 9/2006 | Miller | |
| 7,211,074 B2 | 5/2007 | Sansoucy | |
| 7,224,272 B2 | 5/2007 | White, II et al. | |
| 7,252,649 B2 | 8/2007 | Sherry | |
| 7,297,158 B2 | 11/2007 | Jensen | |
| 7,438,699 B2 | 10/2008 | Pecor et al. | |
| 7,452,374 B2 | 11/2008 | Hain et al. | |
| RE41,448 E | 7/2010 | Squitieri | |
| 7,762,977 B2 | 7/2010 | Porter et al. | |
| 2002/0049403 A1 | 4/2002 | Alanis | |
| 2002/0151761 A1 | 10/2002 | Viole et al. | |
| 2003/0139806 A1 | 7/2003 | Haverkost et al. | |
| 2004/0024442 A1 | 2/2004 | Sowinski et al. | |
| 2004/0069103 A1 | 4/2004 | Matteucci | |
| 2004/0099395 A1 | 5/2004 | Wang et al. | |
| 2004/0147866 A1 | 7/2004 | Blatter et al. | |
| 2005/0137614 A1 | 6/2005 | Porter et al. | |
| 2005/0203457 A1 | 9/2005 | Smego | |
| 2005/0215938 A1 | 9/2005 | Khan et al. | |
| 2006/0058867 A1 | 3/2006 | Thistle et al. | |
| 2006/0064159 A1 | 3/2006 | Porter et al. | |
| 2006/0081260 A1 | 4/2006 | Eells et al. | |
| 2006/0118236 A1 | 6/2006 | House et al. | |
| 2007/0078412 A1 | 4/2007 | McGuckin, Jr. et al. | |
| 2007/0078416 A1 | 4/2007 | Eliasen | |
| 2007/0078438 A1 | 4/2007 | Okada | |
| 2007/0088336 A1 | 4/2007 | Dalton | |
| 2007/0123811 A1 * | 5/2007 | Squitieri | 604/6.16 |
| 2007/0135775 A1 | 6/2007 | Edoga et al. | |
| 2007/0161958 A1 | 7/2007 | Glenn | |
| 2007/0167901 A1 * | 7/2007 | Herrig et al. | 604/6.16 |
| 2007/0173868 A1 | 7/2007 | Bachinski et al. | |
| 2007/0191779 A1 | 8/2007 | Shubayev et al. | |
| 2007/0197856 A1 | 8/2007 | Gellman et al. | |
| 2007/0219510 A1 | 9/2007 | Zinn et al. | |
| 2007/0233018 A1 | 10/2007 | Bizup et al. | |
| 2007/0249986 A1 | 10/2007 | Smego | |
| 2007/0249987 A1 | 10/2007 | Gertner | |
| 2007/0265584 A1 | 11/2007 | Hickman et al. | |
| 2007/0293829 A1 | 12/2007 | Conlon et al. | |
| 2008/0009781 A1 | 1/2008 | Anwar et al. | |
| 2008/0027534 A1 | 1/2008 | Edwin et al. | |
| 2008/0167595 A1 | 7/2008 | Porter et al. | |
| 2008/0306580 A1 | 12/2008 | Jenson et al. | |

FOREIGN PATENT DOCUMENTS

| | | |
|---|---|---|
| DE | 29515546 | 3/1997 |
| EP | 0540834 | 5/1993 |
| JP | 57-14358 | 1/1982 |
| JP | 58-168333 | 11/1983 |
| JP | 62-112567 | 5/1987 |
| JP | 04-507050 | 12/1992 |
| JP | 05-212107 | 8/1993 |
| JP | 06-105798 | 4/1994 |
| JP | 09-84871 | 3/1997 |
| JP | 2003-501223 | 1/2003 |
| WO | WO 84/03036 | 8/1984 |
| WO | WO 95/19200 | 7/1995 |
| WO | WO 96/24399 | 8/1996 |
| WO | WO 00/76577 | 12/2000 |
| WO | WO 01/05463 | 1/2001 |
| WO | WO 2004/112880 | 12/2004 |

OTHER PUBLICATIONS

Alan S. Coulson, M.D., Jagjit Singh, M.D., Joseph C. Moya, "Modification of Venous End of Dialysis Grafts: An Attempt to Reduce Neointimal Hyperplasia," *Dialysis & Transplantation*, vol. 29, No. 1, Jan. 2000, pp. 10 to 18.

Co-Pending Reissue U.S. Appl. No. 10/219,998 and its prosecution history.

A.S. Coulson, M.D., Ph.D., Judy Quarnstrom, I.V.N., J. Moshimia, M.D., "A Combination of the Elephant Trunk Anastomosis Technique and Vascular Clips for Dialysis Grafts,"*Surgical Rounds*, Nov. 1999, pp. 596 to 608.

L.C. Koo Seen Lin et al., "Contemporary Vascular Access Surgery for Chronic Haemodialysis", 1996 The Royal College of Surgeons of Edinburgh, J.R. Coll. Surg. Edinb., 41, June 164-169.

Seshadri Raju, M.D., PTFE Grafts for Hemodialysis Access, "Techniques for Insertion and Management of Complications", Ann. Surg. vol. 206, No. 5, Nov. 1987, pp. 666-673.

Anatole Besarab et al., "Measuring the Adequacy of Hemodialysis Access", Current Opinion in Nephrology and Hypertension 1996, 5:527-531, Rapid Science Publishers ISSN 1062-4821.

Melhem J.A. Sharafuddin, MD et al., Dialysis Access Intervention, "Percutaneous Balloon-assisted Aspiration Thrombectomy of Clotted Hemodialysis Access Grafts", Journal of Vascular and Interventional Radiology, vol. 7, No. 2, Mar.-Apr. 1996, pp. 177-183.

David A. Kumpe et al., "Angioplasty/Thrombolytic Treatment of Failing and Failed Hemodialysis Access Sites: Comparison with Surgical Treatment", Progress in Cardiovascular Diseases, vol. XXXIV, No. 4 (Jan./Feb. 1992): pp. 263-278.

Robert Y. Kanterman, MD et al., Intervention Radiology, "Dialysis Access Grafts: Anatomic Location of Venous Stenosis and Results of Angioplasty", Radiology Apr. 1995, vol. 195, No. 1, 195:135-139.

Co-Pending U.S. Appl. No. 12/688,716, filed Jan. 15, 2010 and its prosecution history including the Amendment filed Dec. 27, 2010.

\* cited by examiner

VASCULAR ACCESS SYSTEM

CROSS-REFERENCE TO RELATED APPLICATIONS

This application claims the benefit of U.S. Provisional Application No. 61/034,125, filed Mar. 5, 2008, which is hereby incorporated by reference herein its entirety. Each of the following applications also is incorporated by reference herein in its entirety: U.S. application Ser. No. 11/600,589, filed Nov. 16, 2006, U.S. application Ser. No. 11/216,536 filed on Aug. 31, 2005, and U.S. application Ser. No. 10/962,200, filed on Oct. 8, 2004.

BACKGROUND OF THE INVENTIONS

1. Field of the Inventions

This application relates to a system for connecting multiple portions of a fluid carrying conduit.

2. Description of the Related Art

In the United States, approximately 400,000 people have end-stage renal disease requiring chronic hemodialysis. Permanent vascular access sites for performing hemodialysis may be formed by creating an arteriovenous (AV) anastomosis whereby a vein is attached to an artery to form a high-flow shunt or fistula. A vein may be directly attached to an artery, but it may take 6 to 8 weeks before the venous section of the fistula has sufficiently matured to provide adequate blood flow for use with hemodialysis. Moreover, a direct anastomosis may not be feasible in all patients due to anatomical considerations. Other patients may require the use of artificial graft material to provide an access site between the arterial and venous vascular systems.

Although many materials that have been used to create prosthetic grafts for arterial replacement have also been tried for dialysis access, expanded polytetrafluoroethylene (ePTFE) is the preferred material. The reasons for this include its ease of needle puncture and particularly low complication rates (pseudo-aneurysm, infection, and thrombosis). However, AV grafts still require time for the graft material to mature prior to use, so that a temporary access device, such as a Quinton catheter, must be inserted into a patient for hemodialysis access until the AV graft has matured. The use of temporary catheter access exposes the patient to additional risk of bleeding and infection, as well as discomfort. Also, patency rates of ePTFE access grafts are still not satisfactory, as the overall graft failure rate remains high. Sixty percent of these grafts fail yearly, usually due to stenosis at the venous end. (See Besarab, A & Samararpungavan D., "Measuring the Adequacy of Hemodialysis Access". *Curr Opin Nephrol Hypertens* 5(6) 527-531, 1996, Raju, S. "PTFE Grafts for Hemodialysis Access". *Ann Surg* 206(5), 666-673, November 1987, Koo Seen Lin, L C & Burnapp, L. "Contemporary Vascular Access Surgery for Chronic Hemodialysis". *J R Coll Surg* 41, 164-169, 1996, and Kumpe, D A & Cohen, M A H "Angioplasty/Thrombolytic Treatment of Failing and Failed Hemodialysis Access Sites: Comparison with Surgical Treatment". *Prog Cardiovasc Dis* 34(4), 263-278, 1992, all herein incorporated by reference in their entirety). These failure rates are further increased in higher-risk patients, such as diabetics. These access failures result in disruption in the routine dialysis schedule and create hospital costs of over $2 billion per year. See Sharafuddin, M J A, Kadir, S., et al. "Percutaneous Balloon-assisted aspiration thrombectomy of clotted Hemodialysis access Grafts". *J Vasc Interv Radiol* 7(2) 177-183, 1996, herein incorporated by reference in its entirety.

SUMMARY OF THE INVENTIONS

In one embodiment, a system is provided for connecting components of an implantable extravascular blood conduit. The blood conduit has a proximal end adapted to couple with a first vascular segment and a distal end adapted to be inserted into a second vascular segment. The system comprises a catheter, which can be configured as an outflow component, and a connector. The catheter has a proximal portion and a distal portion. The distal portion is configured such that when in use the distal portion can freely float within the second vascular segment. The proximal portion comprises an elongate body defining an inner wall having an inner perimeter. The inner wall also defines a blood flow lumen. The proximal portion also includes a braided structure that can be embedded in the catheter body and disposed about the lumen. The connector is used to fluidly couple with the proximal portion of the catheter. The connector has a connector body that has an outer surface defining a first outer perimeter and an inner surface defining a lumen. An engagement feature is disposed on an outer surface of the connector body adjacent a distal end thereof. The engagement feature defines a second outer perimeter greater than the first outer perimeter. The proximal portion of the catheter has a first configuration in the free state wherein the inner perimeter is less than the first outer perimeter of the connector body. The proximal portion of the catheter has a second configuration when in axial compression wherein the braided structure expands to permit the inner perimeter of the catheter body to expand such that the proximal portion of the catheter can be advanced over the engagement feature of the connector body.

In another embodiment, a connector system is provided. The connector system includes an engagement mechanism that includes an engagement feature and a braided reinforcement coupled with a proximal portion of a catheter. The engagement feature can include one, two, or two or more barbs.

In another embodiment, a catheter is provided for insertion into a blood vessel at a vessel insertion site for delivering blood after dialysis to a location downstream of the vessel insertion site. The catheter includes an elongate body and a braided structure. The elongate body has a proximal portion, a distal portion, and a lumen extending therebetween along a longitudinal axis. The elongate body has an inner surface surrounding the lumen and an outer surface surrounding the inner surface. The distal portion of the elongate body defines a cross-sectional area sufficiently small to permit insertion thereof into the blood vessel such that blood flows in the vessel around the distal portion. The braided structure has a proximal end and a distal end. The braided structure can be embedded within the elongate body. In one embodiment, the outer surface of the elongate body completely surrounds the braided structure. The braided structure extends from the proximal portion of the elongate body toward the distal portion thereof. The distal portion of the elongate body and the braided structure are sufficiently flexible such that the catheter can freely float at a vascular location downstream of the vessel insertion site. The proximal portion of the elongate body and the braided structure are configured to respond to an axial force by expanding such that the lumen is enlarged along the longitudinal axis for advancement over an engagement feature for coupling the catheter with another blood conduit.

A kit is provided for accessing blood from a patient's vasculature. The kit includes a catheter, a graft portion, and a connector for interconnecting the catheter and the graft portion. The connector includes an engagement feature configured to radially deform a proximal portion of the catheter. The proximal portion of the catheter includes a reinforcement member that increases the force needed to disconnect the catheter from the connector, such that the force to disconnect is greater than a force to connect the catheter and the connector.

In another embodiment, a method of assembling a blood flow conduit in-situ is provided. The method includes providing a proximal blood conduit portion and a distal blood conduit portion. The distal blood conduit portion includes a catheter in some embodiments. The distal blood conduit can comprise a proximal end portion in which a braided structure is embedded. The method includes cutting the distal blood conduit through the braided structure to size the distal blood conduit in-situ and distal blood conduit the catheter to the proximal blood conduit portion.

BRIEF DESCRIPTION OF THE DRAWINGS

The structure and method of using the invention will be better understood with the following detailed description of embodiments of the invention, along with the accompanying illustrations, in which.

DETAILED DESCRIPTION OF THE PREFERRED EMBODIMENT

Figure 1:
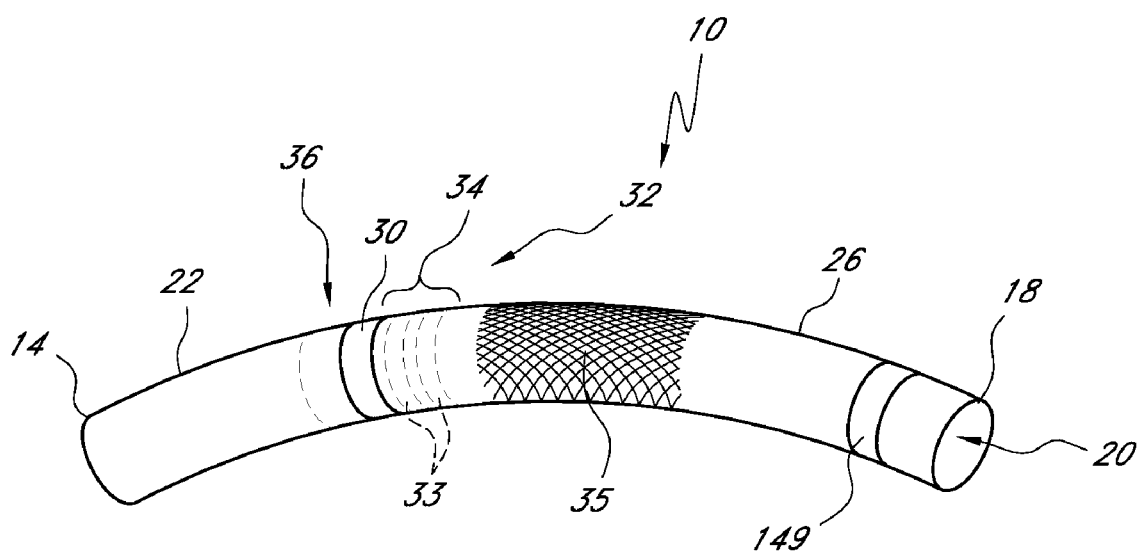
FIG. 1 is a perspective view of a vascular access system having a proximal end adapted to couple with a first vascular segment and a distal end adapted for insertion into a second vascular segment.

This application relates to new vascular access systems, new connector systems, and new fluid-carrying conduits. The fluid carrying conduits are arteriovenous (AV) shunts or catheters in various embodiments. Some of the embodiments described herein may be incorporated into a hemodialysis system.

Hemodialysis treatments and vascular access devices therefore are discussed in greater detail in U.S. patent application Ser. No. 10/962,200 (US Publication No. 2005-0137614-A1), Ser. No. 11/216,536 (US Publication No. 2006-0064159 A1), and Ser. No. 11/600,589 (US Publication No. 2007-0167901 A1) and in U.S. Pat. Nos. 6,102,884 and 6,582,409. The embodiments described herein can be combined with the systems and methods of any of these applications and patents, all of which are hereby incorporated by reference in their entirety.

As will be understood in view of the description herein provided, the new connector systems and apparatuses can improve one or more areas of performance of vascular access systems. For example, the embodiments described herein improve in-situ connection of a catheter, or other blood-carrying conduit, configured for use as an outflow component, to another component or device of a vascular access system.

In some embodiments, a reinforcement member can be incorporated into the vascular access system (e.g., in a proximal portion of a catheter or other blood carrying conduit) to enhance the security of a connection between a catheter and another component of the vascular access system. In some cases, the reinforcement member also extends through a substantial portion of the length of a blood carrying conduit to improves kink and crush resistance of the fluid carrying conduit. These and other advantages of the new devices and methods described herein could be useful in a number of environments that employ a vascular access system, such as vascular access devices, ventricular assist devices, total artificial hearts, and various types of hemodialysis systems.

Environments in which these improvements could be used include short-term applications (e.g., several days to a week) and longer-term application. For example, the improvements described herein are useful in longer-term applications of 30 days or more. The improvements described herein are useful in longer-term applications of 90 days or more. In some cases, the improvements described herein are useful in long-term applications of 1 year or more. The embodiments described herein can be incorporated into short-term and into longer-term applications for dialysis.

As will be discussed below, a braided structure can be incorporated into a fluid-carrying conduit. In some embodiments, the braided structure can be embedded in an elongate body of the fluid-carrying conduit, providing a smooth relatively constant outer surface. The braided structure can improve the security or integrity of the connection between the blood-carrying conduit and other structures to which it is attached. In various embodiments, these innovations provide greater durability and manufacturability. In addition, the implantation process can be enhanced, such as by providing better connectability and, in some cases, a tactile confirmation of the security of a connection, as discussed below. In some cases, a visual confirmation of the security of a connection can be provided.

FIG. 1 depicts one embodiment of a vascular access system 10 that is configured to shunt blood from a first vascular segment to a second vascular segment. The vascular access system 10 can take any suitable form, but preferably the system is adapted to be implanted beneath the skin of the patient. In one embodiment, the vascular access system 10 is implanted primarily extravascularly, though a distal portion thereof may reside in or extend through a blood vessel. The vascular access system 10 can be partly or completely implanted. Various techniques for implanting are discussed below, including placement of at least a portion of the system 10 in a vascular segment. Also, the vascular access system 10 can be implanted in a subcutaneous tunnel, as discussed further below. Additional details of processes for implantation are discussed in the patents and applications listed above, which are incorporated by reference herein.

The vascular access system 10 has a proximal end 14 and a distal end 18 and a lumen 20 that extends between the proximal and distal ends 14, 18. The proximal end 14 can be adapted to couple with, e.g., attached to, a first vascular segment and the distal end 18 can be adapted to be coupled with, e.g., inserted into a second vascular segment. The lumen 20 preferably extends between the proximal and distal ends 14, 18 and provides a pathway for blood to flow between the first and second vascular segments. The lumen 20 also can be accessed from outside the patient to facilitate dialysis or other treatment.

The first and second vascular segments are arterial or venous vascular segments in various techniques. For example, the proximal end 14 can be adapted to be coupled with a brachial artery or other artery that resides close to the skin. Any suitable coupling between the proximal end 14 and the first vascular segment can be used. In one embodiment the proximal end 14 can be attached by an end-to-side anastomosis to a brachial artery. The distal end 18 can be adapted to couple with or extend into a vein, e.g., in the central venous system, as discussed below and in the application incorporated by reference herein.

In one embodiment, the vascular access system 10 includes a plurality of components that can be assembled to form the lumen 20. In one embodiment, a first blood carrying conduit 22 extends from the proximal end 14 toward the distal end 18 and a second blood carrying conduit 26 extends from the distal 18 toward the proximal end 14. In one embodiment a third blood carrying conduit 30 is positioned between the first and second blood carrying conduits 22, 26. As discussed below, the third blood carrying conduit 30 is adapted to connect the first and second blood carrying conduits 22, 26 together in various embodiments.

Where provided, the third blood carrying conduit 30 enables the first and second blood carrying conduits 22, 26 to have different characteristics that are well suited for the unique ways in which these conduits interact with the vasculature. For example, the first blood carrying conduit 22 can be specifically configured to be integrated into the vessel with which it is coupled, e.g., by anastomosis connection to an artery. Also, the second blood carrying conduit 26 can be specifically configured to interact with a vascular segment to minimize the likelihood of adverse side effects, e.g., by being flexible or otherwise formed to enable a distal portion of the conduit 26 to extend into the central venous system and interact in an atraumatic manner with vessel walls and other tissues in the vasculature or heart. Thus, this innovation pertains to the unique requirements of a device that perform both as a permanently implanted extravascular graft and as an intravascular catheter.

The vascular access system 10 can be configured with an engagement mechanism 32 that enhances the security of a connection between two blood carrying conduits of the system. The engagement mechanism 32 can include multiple portions with at least one portion located on the second blood carrying conduit 26 and at least one portion is located on the third blood carrying conduit 30. In some embodiments, the engagement mechanism 32 is configured such that the connection formed thereby requires a greater force to disconnect than is required to connect the second and third blood carrying conduits 26, 30. This provides greater security of and confidence in the connection at the engagement mechanism 32.

In various embodiments, the engagement mechanism 32 includes an engagement feature 33 located on one of the second and third blood carrying conduits 26, 30 and an enlargeable portion 34 on the other of the second and third blood carrying conduits 26, 30. For example, as discussed in more detail below, the third blood carrying conduit 30 can include at least one barb and the second blood carrying conduit 26 can be formed to apply an inward and sometimes distally directed force on the barb to resist disconnection of the conduits. In one embodiment, a distal portion of the third blood carrying conduit 30 includes two barbs. In one embodiment, the second blood carrying conduit 26 includes a braided structure or other expandable reinforcement member 35 that generates a compressive force on the barb or barbs to enhance the security of the engagement mechanism 32. FIG. 1 only shows the braided structure partially for clarity. As discussed further below, the braided structure can extend to the proximal end 14 and toward the distal end 18. Various additional examples of features of engagement mechanisms are discussed below.

In some embodiments, the vascular access system 10 also includes an engagement mechanism 36 that facilitates coupling the first blood carrying conduit 22 with a distal portion of the lumen 20. As discussed further below, the engagement mechanism 36 can be incorporated into a proximal portion of a connector. In other embodiments, the first and third conduits 22, 30 can be unitary in construction such that the engagement mechanism 36 is not required.

The first blood carrying conduit 22 can take any suitable form for providing fluid communication between a patient's vascular system and the lumen 20. In one form the first blood carrying conduit 22 is a graft formed of a suitable material, e.g., ePTFE. In some applications, it is desirable to provide access to the lumen 20 very soon after implantation of the system 10. Various features for enabling access very soon after implantation, if not immediately thereafter, are discussed in the applications incorporated by reference herein above, including U.S. applications Ser. No. 11/216,536 (US Publication No. 2006-0064159 A1) and Ser. No. 11/600,589 (US Publication No. 2007-0167901 A1). Other suitable biocompatible materials can be used and these will be apparent to one skilled in the art.

Although illustrated in an AV shunt context, the engagement mechanism is also relevant to other context. Accordingly, the first blood carrying conduit 22 could be a proximal portion of a connector, or a component of another system that conveys blood, e.g., in a ventricular assist device.

In one embodiment, the second blood carrying conduit 26 is configured as a catheter for returning blood to a patient's vasculature. In some embodiments, the conduit 26 is an outflow component of the system 10. The catheter preferably is adapted such that, in use, at least a distal end portion thereof can freely float within a vascular segment when the vascular access system 10 is applied to a patient. This feature reflects research that indicates that graft failures from localized stenosis at the venous end of AV grafts are primarily due to intimal hyperplasia, compliance mismatch between the graft and the native vein anastomosis, and turbulent flow at the anastomosis site. Kanterman R. Y. et al "Dialysis access grafts: Anatomic location of venous stenosis and results of angioplasty." Radiology 195: 135-139, 1995. We hypothesize that these causes could be circumvented by eliminating the venous anastomosis and instead, using a fluid carrying conduit to discharge the blood directly into the venous system. We have developed vascular access system that eliminates the venous anastomosis in the AV shunt, using a catheter element at the venous end and a synthetic graft element anastomosed to the artery in the standard fashion. We believe that such system should eliminate or reduce venous hyperplasia, which is the largest reason for AV shunt failure.

Accordingly, configuring the second blood carrying conduit 26 (e.g., a distal portion thereof) to freely float provides atraumatic interaction with the blood vessel. Such a configuration also can minimize the likelihood of damage to the vessel in which the distal end portion resides by minimizing trauma to the vessel.

In some embodiments, the conduit 30 or portions thereof can be integrated into another component, e.g., into the first blood carrying conduit 22. Thus, the system 10 can be configured with less than three, e.g., only two, separate blood carrying conduits. Additionally, the primary function of the third blood carrying conduit 30 is to couple the first and second blood carrying conduits 22, 26 and thus the third blood carrying conduit need not be exposed to blood or form a part of the lumen 20 in all embodiments.

Figure 2:
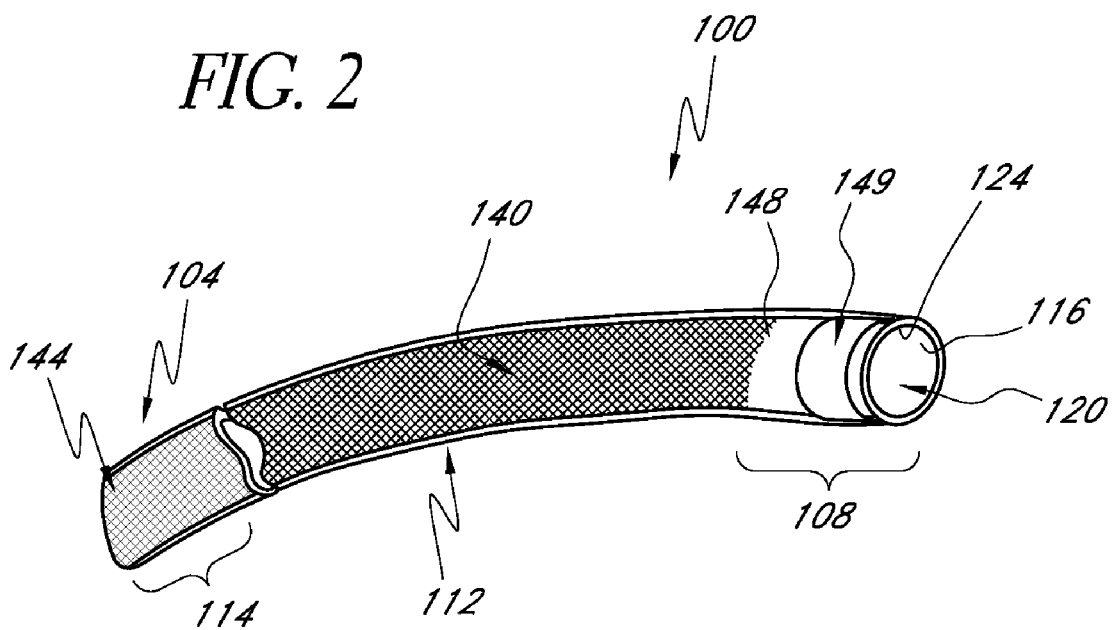
FIG. 2 is a perspective view of a catheter that has a distal portion adapted for positioning in a blood vessel and a proximal portion configured to provide an enhanced connection to another blood conduit.

FIG. 2 shows one embodiment of a catheter 100 that can be used in the vascular access system 10. As used herein "catheter" is a broad term that includes any blood carrying conduit that can be at least partially inserted into a blood vessel and advanced therein to a selected location, including into the atrium. The catheter 100 can take any suitable form, consistent with the below description. In some embodiments, the catheter is configured as an outflow component.

The catheter 100 has a proximal portion 104, a distal portion 108, and an elongate body 112 that extends therebetween. In some applications, the catheter 100 is configured such that the proximal portion 104 is connectable over a barb, as discussed below, to enhance securement of the catheter 100 to a connector, which can be incorporated into the conduit 30. The proximal portion 104 preferably also is trimmable such that the length of the catheter 100 can be determined in-situ. In one embodiment, the catheter 100 also has a sizing region 114 that facilitates customizing the size of the catheter 100 to the patient. In one embodiment, the sizing region 114 is located in the proximal portion 104 of the catheter 100. As will be discussed further below, the sizing region 114 can be trimmed or cut through to reduce the length of the catheter 100. Preferably the sizing region 114 is configured to be cut by hand using any standard cutting implement that would be present in the operating room, such as surgical scissors.

The elongate body 112 preferably defines an inner wall 116 that surrounds a blood flow lumen 120. The inner wall 116 has an inner perimeter 124 that in part defines the blood flow capacity of the catheter 100. In one embodiment, the blood flow lumen 120 is substantially cylindrical and the inner wall 116 and the inner perimeter 124 define are substantially circular in cross-section. In one embodiment, the blood flow lumen 120 has an inner diameter of about 5.0 mm. Lumens of other shapes can be used as well, as will be understood by one skilled in the art. Forming the lumen 120 to have a 5.0 mm diameter lumen provides a benefit of being able to handle sufficient blood flow for dialysis while permitting the outer size of the catheter 100 to be small enough to be insertable into the internal jugular vein in one technique. The outer size and inner perimeter 124 of the catheter 100 can be substantially constant through the length of the lumen 120 or can vary as will be understood by one skilled in the art.

The elongate body 112, particularly the inner wall 116 can be configured to provide adequate hemocompatibility such that blood flowing therethrough is not damaged or adversely affected thereby. The blood flow lumen 120 preferably is configured to convey blood in a substantially atraumatic manner between the portions 104, 108. In one embodiment the inner wall 116 is sufficiently smooth in surface finish to minimize turbulence at the wall. If the catheter 100 is integrated into the vascular access system 10 (e.g., as the second blood carrying conduit 26), the lumen 120 can form a portion of the lumen 20. Other portions of the lumen 20 can be defined in one or both of the first and third blood carrying conduits 22, 30.

The catheter 100 preferably is configured such that in use the distal portion 108 can freely float within a vascular segment. As discussed elsewhere herein, the system 10 can be applied such that the distal portion 108 is positioned in, extends within, or is inserted through a blood vessel, e.g., in the central venous system. Accordingly, the distal portion 108 preferably is configured to have a smaller outer size than the vessel in which it resides. This enables blood to pass around the distal end portion 108. For example, the distal portion 108 can reside in the central venous system in such a manner that blood flows between an outer surface of the distal portion 108 and an inner surface of the blood vessel. In one embodiment, the distal portion 108 of the catheter 100 has an outer perimeter that is substantially circular with an outer diameter of about 6.1 mm. In comparison, the typical vessel through which the distal portion 108 can be inserted is about 8-20 mm. Although larger catheters can be used for some patients and for some other applications, 6.1 mm is a size that is particularly well suited for insertion into an internal jugular vein of an adult human patient. Smaller catheters can be used for certain techniques, e.g., for more peripheral applications.

The dimensions of the system 10 and the components described herein that can be used in the system 10 are not limiting. Rather the dimensions provide examples of specific embodiments. For other applications, other dimensions may be appropriate. For example, the outer diameter of the distal portion 108 of the catheter 100 need not be 6.1 mm but rather would be a function of the vessels into which it is to be inserted. In other applications currently contemplated, the outer diameter of the distal portion 108 could be about four mm to about 8 mm.

Additionally, as discussed below, the distal portion 108 preferably is formed to be relatively flexible. The flexibility permits the distal portion 108 to relatively gently interact with the blood vessel in which it resides. In one application, the catheter 100 is applied through a superficial vessel and is advanced through the internal jugular vein toward the heart. In this environment, a relatively low stiffness construction is sufficient for delivery of the distal portion 108 the catheter 100.

Figure 2A:
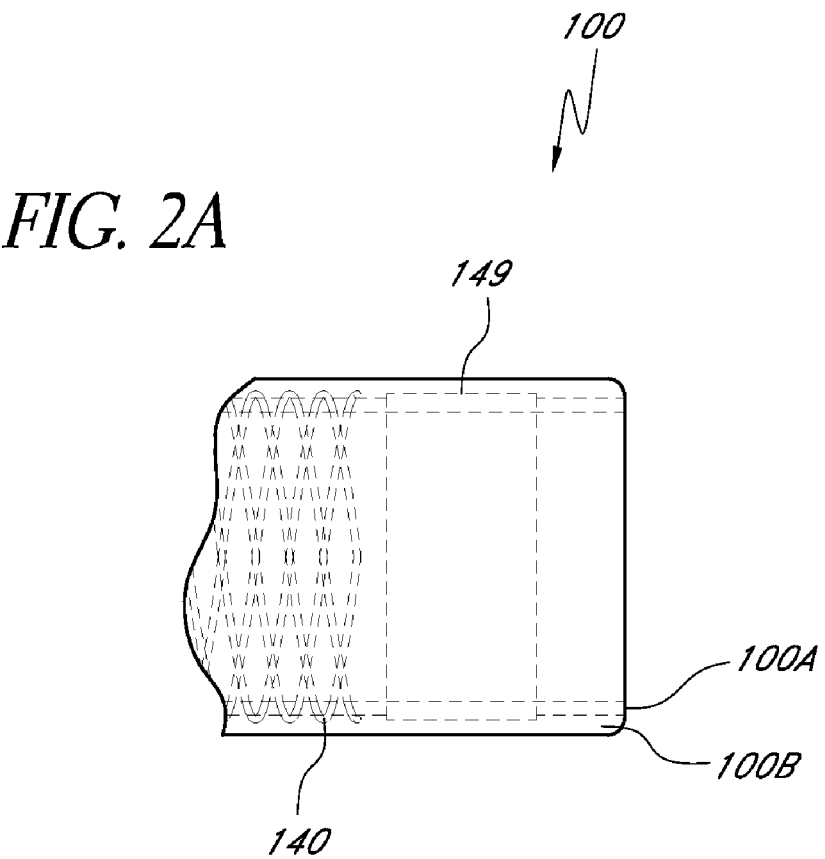
FIG. 2A is a schematic view of a distal portion of the catheter illustrating techniques for embedding a braided structure therein.

FIG. 2A illustrates one approach to making the catheter 100 more flexible in which a soft material is incorporated into the elongate body 112. In various embodiments, all or a portion of the elongate body 112 can be formed of any suitable flexible elastomer, such as polyurethane, CFlex, SIBS (styrene isoprene butadiene) or polyolephins. In one example, silicone tubing can be used in an inner portion 100A of the catheter 100. More generally, the elongate body 112 can be formed of an implantable thermoplastic elastomer. In one embodiment, silicone tubing has a durometer of about 50 Shore A or less is used to form the inner portion 100A of the catheter 100. In some applications, the catheter 100 can be formed of a material having a durometer of 30-80 Shore A will perform adequately. In other embodiments, a higher or lower durometer material can be used. As further discussed below, there can be particular advantages to the softer durometers of 30-60 Shore A and 40-50 Shore A. As discussed further below, an outer portion 100B of the catheter 100 can be formed of a similar or the same material as the inner portion 100A.

In various embodiments, the base material preferably is flexible and base material strength is less critical. In this application, the ability for the braided tubing to expand radially over a connector barbs is preferred. As mentioned previously this is an advantage of a braided reinforcement over a single filament, coiled reinforcement, which cannot expand to slip over a barb. This is similarly an advantage of braid reinforced tube using a softer base material (such as one with a relatively low durometer, e.g., <70 Shore A) over one with a harder base material. Forcing a braided tube with a hard base material over a barb would require an unacceptably high force. Furthermore, under the forces anticipated to be applied during in use, a braided tube with a harder base material would not provide the degree of necking that is desirable in some clinical situations.

The catheter 100 also can include a braided structure 140 or other reinforcing member between the inner portion 100A and the outer portion 100B. The braided structure 140 provides a number of benefits to the catheter 100. For example, the braided structure 140 can be configured to contribute to at least in part, resistance to radial compression of the elongate body 112. Also, the braided structure 140 can be configured to provide at least in part, resistance to kinking of the elongate body 112.

In one embodiment, the braided structure 140 is provided primarily to enhance the security of a connection between the catheter 100 and another component of a blood carrying system, such as the vascular access system 10. For example, the braided structure 140 can enhance the security of an engagement mechanism of which the braided structure forms a part.

In one embodiment, the braided structure 140 includes a proximal end 144 and a distal end 148. The braided structure 140 can be disposed about the lumen 120, e.g., substantially or completely surrounding the lumen. The braided structure 140 also can extend along the lumen 120 such that the proximal end 144 is within the proximal portion 104 of the elongate body 112 and the distal end 148 is within the distal portion 108 of the elongate body. In one embodiment, the braided structure 140 is configured such that the proximal end 144 extends to or adjacent to the proximal end of the elongate body 112.

In one embodiment, the braided structure 140 is configured such that the distal end 148 is located proximal of the distal end of the elongate body 112. For example, the distal end 148 of the braided structure 140 can be located about 0.2 inches, about 0.25 inches, or from about 0.2 to about 0.25 inches proximal of the distal end of the catheter 100. This arrangement permits a device for visualization to be located distal of the distal end 148 of the braided structure 140. For example, a radiopaque marker 149 can be located in the distal portion 108 of the elongate body. In one embodiment, the radiopaque marker 149 is a ring formed of platinum iridium or another radiopaque material. Any other suitable device to provide the clinician with an indication of where the distal portion 108 of the catheter 100 is located when the blood flow conduit is being advanced in the vasculature can be used instead of the radiopaque marker 149 as will be understood by those skilled in the art.

Also, the configuration of the braided structure 140 can be varied along the length of the catheter to optimize certain performance metrics of the catheter. For example, as discussed herein, the distal portion 108 preferably is relatively flexible to minimize trauma to the patient's vasculature. This can be achieved by varying the pic count of the braided structure 140. Additionally, a proximal portion of the braided structure 140 can be optimized to enhance the connection strength of an engagement mechanism as discussed herein.

FIG. 2A illustrates that the braided structure 140 can be embedded in the elongate body 112. In one embodiment, the braided structure 140 is embedded in the elongate body 112 such that an outer surface of the elongate body 112 surrounds the braided structure 140. In some cases, the braided structure 140 is disposed within the elongate body 112 such that the outer surface of the elongate body 112 is substantially smooth along the longitudinal axis of the catheter body. When embedded in the elongate body 112, the braided structure 140 also can be disposed radially outside of the inner wall 116 of the elongate body 112. The braided structure 140 also can be disposed radially between the inner wall 116 of the elongate body 112 and an outer surface thereof.

Although the catheter 100 is relatively soft, the braided structure 140 provides reinforcement that prevents or substantially minimizes kinking, crushing, and other phenomenon that can cause at least partial collapse of the lumen 120. Collapse of the lumen 120 can occur when the catheter 100 traverses a bend of relatively small radius. For example, in some applications the catheter 100 is required to traverse a joint, such as the shoulder of a patient. Such a traverse could require a relatively small bend radius. In other applications, the catheter 100 need not traverse a small bend radius (e.g., when not crossing a joint). In some applications, a preferred routing of the catheter 100 may cause the conduit to traverse a bend with a radius of about 1.0 inch. In some applications, a preferred routing of the catheter 100 may cause the conduit to traverse a bend with a radius of 1.0 inch or more. In other applications, in a preferred routing the catheter 100 may have to traverse a bend with a radius of about 0.25 inch. In other applications, in a preferred routing the catheter 100 may have to traverse a bend with a radius of about 0.5 inch. In other applications, in a preferred routing the catheter 100 may have to traverse a bend with a radius of between about 0.25 inch and about 1.0 inch. In all of these cases, the braided structure 140 provides a reinforcement to prevent or substantially minimize collapse of the lumen 120.

Properties of the braided structure 140 and variations thereof result in desirable kink minimizing properties not achievable using a coil reinforcement. At very small bend diameters, the braided structure 140 is expected to gradually flatten, instead of suddenly inflecting to a kinked configuration. This is advantageous for several reasons. First, gradual flattening of the braided structure 140 will be detectable by a clinician (e.g., using an imaging technology such as X-Ray imaging) such that the clinician can recognize that a less than desirable bend radius is present before full narrowing of the blood conduit occurs. Secondly, a coil reinforcement undergoes higher strain levels and alternating strains than the braided structure 140. This prevents or delays undesirable fracture or failure due to repeated flexure at very small bend radii. In addition, only a fraction of the plurality of members in the braided structure 140 undergo significant stress or strain level at minimum bend radii. The braid members on the top and bottom of the fold undergo negligible stress compared to the members at the sides of the fold. This means that even if the loading conditions were severe enough to fracture braid members on the sides of the fold, the majority of braid members at the fold would not fracture and the device would remain substantially intact. In previous single filament, coil reinforced devices, any fracture was potentially catastrophic. Also, the disclosed braid configurations advantageously exhibit full narrowing or kinking at a much smaller bend radii than prior coil reinforced devices. Prior coil reinforced devices had a kink radius of approximately 0.5 inch, whereas various embodiments of the catheter 100 have a kink radius of approximately 0.2 inches.

In some embodiments, the braided structure 140 forms a part of an engagement mechanism, similar to the engagement mechanism 32.

Figure 3:
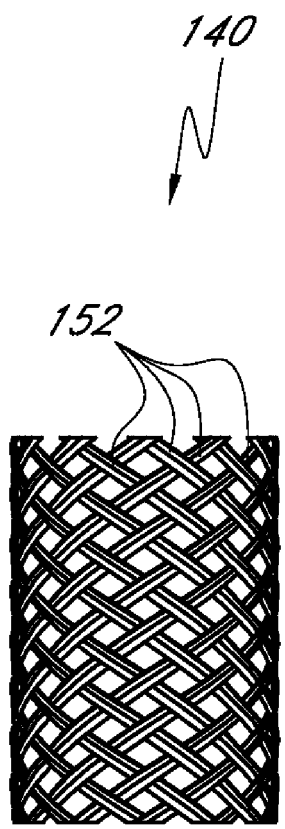
FIG. 3 is a side view of a reinforcement member configured to be incorporated into the blood flow conduit of FIG. 2.

FIG. 3 illustrate further details of one embodiment of the braided structure 140. In one embodiment, the braided structure 140 has a plurality of braid members 152 that overlap each other in the structure. The braided structure 140 can comprise a shape memory material, such as a nickel titanium alloy (e.g., a NITINOL® alloy) in various embodiments. Other suitable materials include stainless steel (e.g., 304 or 316), titanium, glass, Kevlar and other similar fibrous materials. For example, each of the braided members 152 can comprise a nickel titanium alloy or other shape memory material. In some embodiments, the braided members 152 are woven together to form the braided structure 140. The braid members 152 can have a cross-section with a first transverse dimension D1 being greater than a second transverse dimension D2, the first transverse dimension D1 being perpendicular to the second transverse dimension D2. In one embodiment, the second transverse dimension D2 (e.g., the shorter of the two dimensions) is generally radially extending relative to the longitudinal axis of the lumen 120. These embodiments are illustrated by FIG. 3A.

Such an arrangement can minimize the thickness of the elongate body 112 between the inner wall 116 and the outer surface of the elongate body. This can result in a very thin structure, e.g., with a thickness of about 2.0 mm or less. In one embodiment, the thickness of the catheter 100 between the inside wall 116 and an outer surface of the catheter is about 1.1 mm. In one embodiment, the thickness of the braided member 152 is less than about 50 percent of the thickness of the elongate body 112. In one embodiment, the thickness of the braided member 152 is less than about 25 percent of the thickness of the elongate body 112. In one embodiment, the thickness of the braided member 152 is about 10 percent of the thickness of the elongate body 112. Minimizing the thickness of the wall of the catheter is important in some embodiments because it can maximize the size of the lumen for carrying blood while still maintaining the ability to insert the catheter 100 into selected vessels.

By reducing the dimension D2, the crossing profile of the catheter 100 can be reduced or minimized. Reducing the crossing profile provides an advantage of permitting access to the vascular system through a smaller incision. In some embodiments, by reducing the dimension D2, the size of the lumen 120 can be increased for a given crossing profile. Increase in the size of the lumen 120 is advantageous in that it permits greater fluid carrying capacity in the lumen. The braided structure 140 provides considerable kink and crush resistance and relative flexibility of the elongate body 112.

Figure 3A:
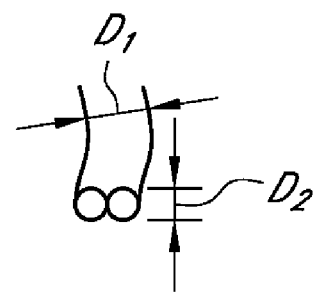
FIG. 3A is an end view of one braided member of the braided structure of FIG. 3.

One embodiment illustrated by FIG. 3A provides a plurality of braided members 152 that have elongate cross-sections provided by a plurality of axi-symmetric side-by-side wires. For example, a braided member could include two circular cross-section wires provided in a side-by-side arrangement. In this embodiment, the radial dimension (D2) of the braided members 152 is about equal to the diameter of the wires and the dimension transverse to the radial dimension (D1) is about equal to twice the diameter of the wires. One useful construct for the braided members 152 incorporates two 0.005 inch wires that are formed of a nickel titanium alloy. Other embodiments could incorporate 0.006 inch or larger wires. Some embodiments could incorporate 0.004 inch or smaller wires. Larger wires may be suitable for larger catheters or for catheters that can use smaller lumens. Smaller wires may be suitable for smaller catheters or for catheters subject to less crush or kink forces. In other embodiments, the braided members 152 can be formed with one or more flat or oval cross-section wires. A suitable alloy would include 56 weight % nickel and 44 weight % titanium. This material can be treated to provide suitable properties, such as by a straight annealing. A light oxide finish is suitable for some embodiments.

Any suitable woven pattern can be provided for creating the braided structure 140. For example, a hopsack weave can be employed in which the braided members 152 cross over a first transverse braided member then cross under a second transverse braided member adjacent the first transverse braided member. This pattern can be repeated throughout the braided structure 140 to provide a suitable weave. Hopsack weave is sometimes referred to as a diamond pattern full load. In other embodiments, the weave could be a diamond pattern half-load or a herringbone weave, which will be understood by one skilled in the art. Other weave arrangements that can be used include a linen weave, for example. However, for some applications, the linen weave is not expected to perform as well as other weave patterns discussed herein.

Further aspects of the braided structure 140 can affect its performance. For example, the density and configuration of the braided members 152 can affect the degree of security when the catheter 100 is engaged with another blood carrying component. For example, in one embodiment, the braided structure 140 is formed with a suitable helix angle, which is defined as the angle between any of the braided members 152 and a longitudinal axis of the braided structure 140. A helix angle within a range of about 40 degrees to about 65 degrees could be used in some embodiments of the braided structure 140. In other embodiments, the braided structure 140 can be formed with a helix angle in the range of about 50 degrees to about 55 degrees. In one embodiment the braided structure 140 defines a helix angle of about 51 degrees. In one embodiment the braided structure 140 defines a helix angle of about 54 degrees. A higher helix angle creates a more flexible catheter. A lower helix angle provides less flexibility but is easier to advance over a connector as discussed below. Lower helix angle also provides a less crush resistant catheter, which is less optimal in some applications.

Another aspect of the braided structure 140 that relates to the performance of the engagement mechanism 32 of which the braided structure may be a part is the pic count (crossings per unit length) of the braided structure 140. One skilled in the art will recognize that pic count and helix angle are related. More particularly, pic count can affect the connectability of the catheter 100 with a connector, which can form a part of the third blood carrying conduit 30. Greater pic count corresponds to a higher force required for coupling the engagement mechanism 32. Lesser pic count corresponds to lower connecting forces. Catheters with lower pic counts are more subject to kinking. In one embodiment, the braided structure 140 has a pic count between about 21 ppi and about 24 ppi. In another embodiment, the braided structure 140 has a pic count of between about 22-24 ppi when assembled on the catheter 100. In another embodiment, the braided structure 140 has a pic count of about 21 ppi. In another embodiment, the braided structure 140 has a pic count of about 23 ppi. In another embodiment, a pic count of 22 ppi would be suitable.

Figure 7:
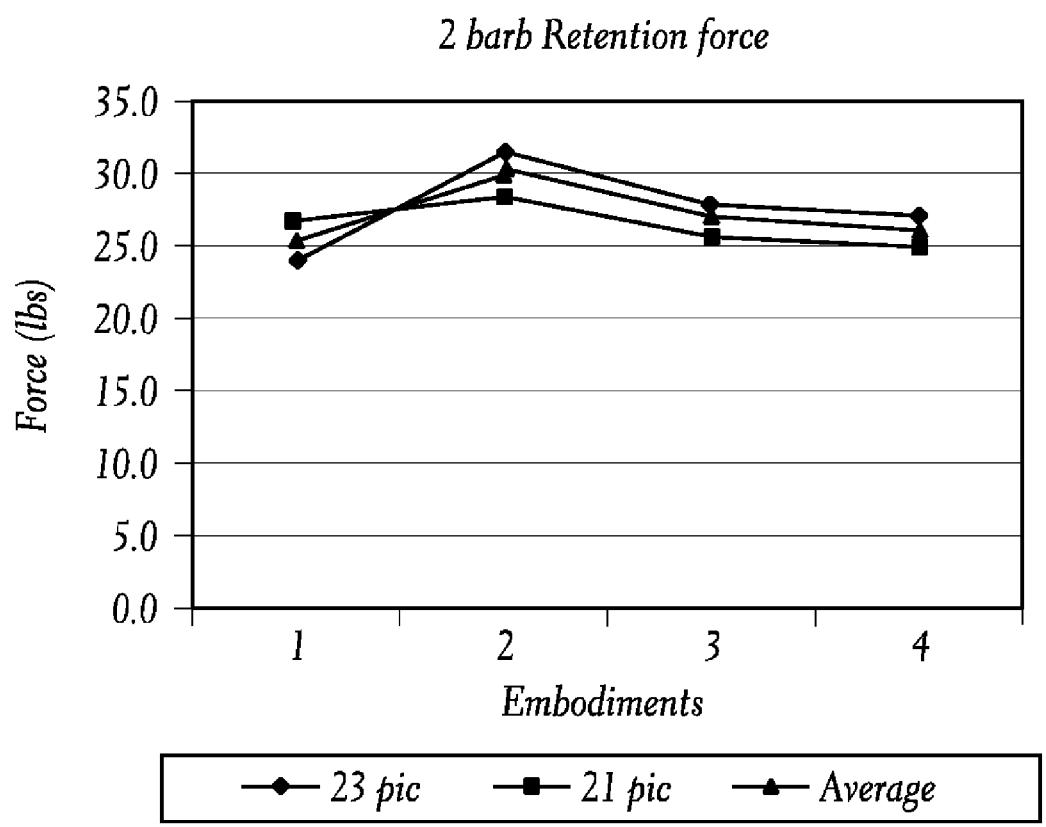
FIG. 7 is a graph illustrating a retention force for an engagement mechanism having a braided structure with different pic counts.
Figure 8:
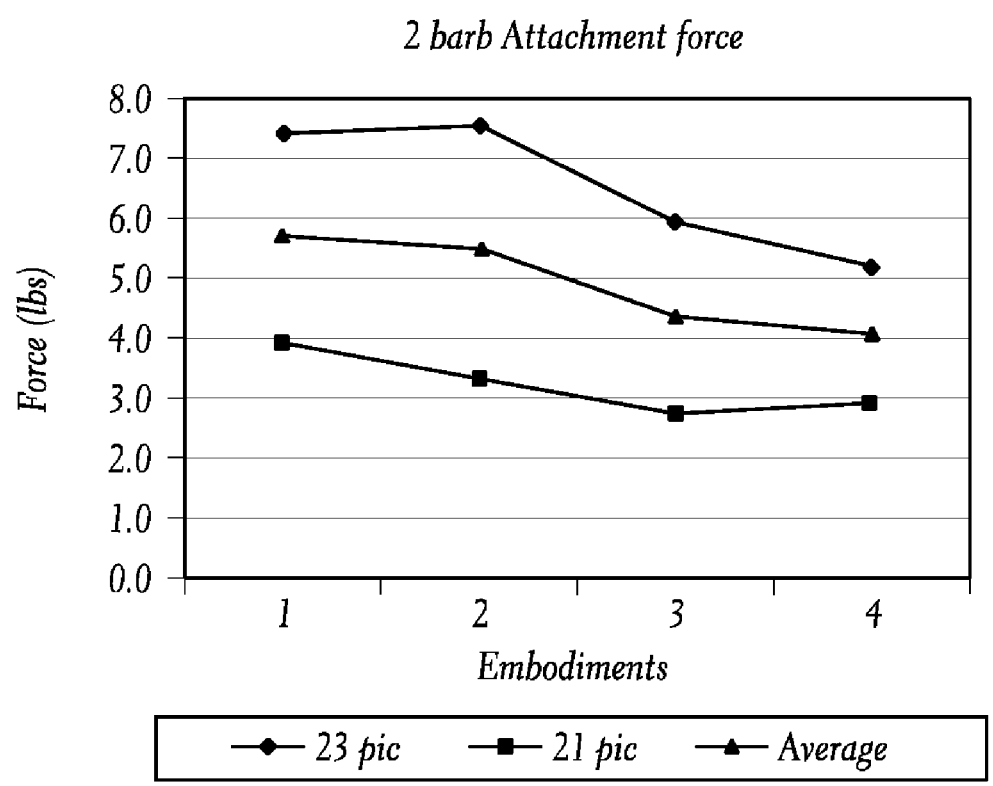
FIG. 8 is a graph of attachment forces for various embodiments.

FIGS. 7 and 8 illustrate a comparison of the retention force and attachment force respectively for various embodiments of an engagement mechanism. In this study, pic count of a braided structure in a catheter and various aspects of the engagement feature 240 of the connector 200 were varied.

The variables that were varied in the connector 200 are shown in the table below, with all dimensions being in inches):

|  | Length of Barb 244 | Length of Barb 248 | Spacing Between Barbs 244 and 248 | Height of barb 244 | Height of barb 248 |
| --- | --- | --- | --- | --- | --- |
| Embodiment 1 | 0.065 | 0.065 | 0.240 | 0.012 | 0.012 |
| Embodiment 2 | 0.065 | 0.05 | 0.225 | 0.012 | 0.011 |
| Embodiment 3 | 0.065 | 0.05 | 0.240 | 0.012 | 0.011 |
| Embodiment 4 | 0.065 | 0.04 | 0.240 | 0.012 | 0.009 |

FIG. 8 shows a general trend to lower attachment forces for Embodiment 4 compared to other embodiments. Embodiment 4 had lower values for the height and the length of the barb 248. Also, FIG. 8 shows that a lower pic count of the braided structure of the catheter can result in a significantly lower attachment force compared to a higher pic count arrangement, where the connector has two barbs. Lowering the attachment force is desirable in some embodiments to provide faster and easier assembling of a vascular access system in-situ for the clinician.

FIG. 7 shows that for the embodiments described in the table above, retention force (e.g., the force needed to disconnect the catheter 100 from the connector 200) was not highly dependent on pic count for the embodiments of the connector studied. Although there is an increase in retention force for Embodiment 2 compared to the other embodiments, all four embodiments had relatively high retention forces compared to an engagement mechanism including a connector with a single barb engaged with a catheter having a braided structure.

Also, the performance of the braided structure 140 can relate to the number of wires incorporated into the weave. In some embodiments, the braided structure 140 includes about forty-eight braided members 152. Other numbers of braided members 152 can be provided, however. For example, in one embodiment, twenty-four braided members 152 can be provided. Fewer wires provide less crush and kink resistance. More wires provide greater resistance in the braided structure 140 to kinking and crushing. Other numbers of wires for forming the braided structure 140 can also be used, as will be understood by one skilled in the art.

Techniques for Forming Blood Carrying Conduits

Various techniques are contemplated for forming the catheter 100 with inner and outer portions 100A, 100B. In some techniques, the outer portion 100B is formed in a different process than the inner portion 100A. For example, the in a first step of one embodiment, an elongate tubular section of silicone or a flexible elastomer is slid onto a solid mandrel to provide the inner portion 100A. The tubular section can have a durometer of about 50 shore A or any other suitable hardness as discussed herein. The tubular section optionally is loaded with barium sulphate. In one technique, the inner diameter of the tubular section is about 5.0 mm and the outer diameter of the tubular section is about 5.5 mm.

Thereafter, the braided structure 140 can be placed over the outer surface of the inner portion 100A. The braided structure 140 can have a diameter of about the same as that of the tubular section outer diameter. In one embodiment, the braided structure 140 has an inner diameter of about 5.5 mm. In one embodiment, the braided structure 140 has an inner diameter of slightly less than the outer diameter of the tubular section. For example, an inner diameter of about 5.4 mm for the braided structure 140 would be suitable. This arrangement causes the braided structure 140 to cinch down on the outer surface of the tubular section forming the inner portion 100A. In one technique, the braided structure 140 is sized such that its length is substantially the same as or slightly less than that of the tubular section.

Thereafter a platinum iridium marker band (or visualization device of other configuration) is positioned over the inner portion 100A. This can be achieved by sliding the marker band over the distal end to a location between the distal end of the braided structure and the distal end of the tubular section. In another technique, strands of the braided structure 140, particularly strands located in the distal portion thereof, can be configured to be visible using radiography or another similar technique.

Thereafter, the assembly formed to this point in the process can be covered with a suitable material to form the outer portion 100B of the catheter 100. For example, the assembly can be coated with a suitable material to form the outer portion 100B of the catheter 100. In one technique, the outer portion 100B is formed by dip or spray coating silicone, polyurethane or other suitable material over the assembly. In another technique, the outer layer can placed over the assembly and bonded, shrunk, thermally fused or otherwise formed together. In another technique, the outer layer can be formed by in-line extrusion over the assembly.

Other optional steps can thereafter be performed in various embodiments. For example, the construct can be cut to size and luer fittings (or other suitable connectors) can be formed on a proximal end thereof as needed. The forgoing steps are illustrative and need not be performed in the order recited.

Engagement Features & Mechanisms

As discussed above, in various embodiments, the braided structure 140 extends to the proximal portion 108 of the catheter 100. At least the portion of the braided structure 140 that so extends can interface with the blood carrying conduit 30 forming a part of the engagement mechanism 32.

Figure 4:
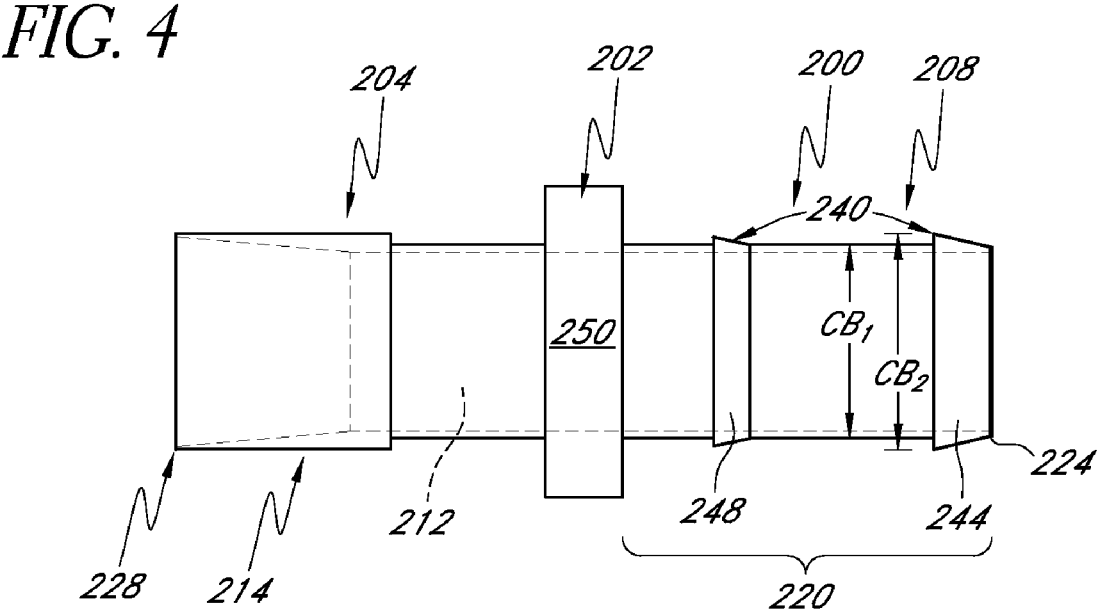
FIG. 4 is a plan view of a connector that is adapted to couple a first blood flow conduit with a second blood flow conduit.

FIG. 4 illustrates one embodiment of a connector 200 that can be incorporated into the blood carrying conduit 30 of the system 10. The connector 200 includes a connector body 202 that has a proximal portion 204, a distal portion 208, and lumen 212 extending therebetween. The lumen 212 can take any suitable form. In one embodiment, the lumen 212 includes a tapered section similar to that described in U.S. application Ser. No. 10/962,200.

The proximal portion 204 preferably is configured to interface with, e.g., be coupled to, the blood carrying conduit 22. The connection between the connector 200 and the conduit 22 can be achieved in any suitable manner. For example, the proximal portion 204 can have an enlarged portion 214 over which the conduit 22 can be advanced. The enlarged portion 214 can comprise a portion of the engagement mechanism 36. Other techniques and structures for connecting the connector 200 and the conduit 22 are described in the applications incorporated by reference herein above, including U.S. applications Ser. Nos. 11/216,536 and 11/600,589.

The distal portion 208 is configured to interface with the blood carrying conduit 26 or with the catheter 100. In one embodiment, the distal portion 208 includes an outer surface 220 that extends between a distal end 224 and a proximal end 228 of the connector 200. In one embodiment, the outer surface 220 extends from the distal end 224 to a proximal end of the distal portion 208, adjacent to an enlarged segment 250. The connector 200 also includes an engagement feature 240 that is disposed on the outer surface 220. In one embodiment, the engagement feature 240 comprises a portion of an engagement mechanism.

The engagement feature 240 can take any suitable form. For example, in one embodiment, the connector body 202 has a first outer size CB1 and the engagement feature 240 has a second outer size CB2 that is greater than the first outer size CB1. The outer sizes CB1, CB2 can correspond to diameters in one embodiment, but could correspond to outer perimeters. In one embodiment, CB1 is a diameter of about 5.4 mm. In one embodiment, CB2 is a diameter of about 6.0 mm. As discussed above, the inner diameter of the catheter 100 is about 5.0 mm in one embodiment. This corresponds to a prestressing of about 1 mm in the diameter of the catheter 100. In some embodiments, a prestressing of about 20% of the inner diameter of a catheter being inserted over the engagement feature 240 can provide suitable connectability. In some embodiments, a suitable amount of prestressing (e.g. enlargement of the inner diameter of a catheter connected over the engagement feature 240) can range from 16-24%. In other embodiments, a suitable amount of prestressing (e.g. enlargement of the inner diameter of a catheter connected over the engagement feature 240) can range from 8-28%.

Prestressing, or stretching the inner size of the catheter 100 creates an enhanced security of the connection formed by the engagement mechanism 32. In particular, the braided structure 140 and the proximal portion of the catheter 100 expand upon being placed in compression during the distal advancement of the connector 200 relative to the catheter. After advancement, the braided structure 140 seeks to return to its pre-formed shape, which produced an inwardly directed force on the connector 200 increasing the security of the engagement between the connector 200 and the catheter 100. Also, the configuration of the braided structure 140 is such that if a force for disconnecting the connector 200 and the catheter 100 is applied, the braided structure will increase the inwardly directed force further securing the connection. This action at the engagement mechanism is analogous to a Chinese finger trap toy, which reduces in cross-sectional size upon elongation.

Providing one or more barbs creates an even more secure connection. In some embodiments, the engagement feature 240 includes a barb 244 that extends over a portion of the connector body 202. The barb 244 can include any structure that includes a raised surface that extends to above the connector body.

FIG. 4 illustrates that in one embodiment a second barb 248 is provided between the first barb 244 and the proximal portion 204 of the connector 200. As discussed below, the second barb 248 of the engagement feature greatly enhances the security of the connection between the catheter 100 and the connector 200. The second barb 248 can take any suitable form. In some embodiments of the connector 200, the second barb 248 is smaller than the first barb 244. For example, the second barb 248 can be about 5.8 mm in diameter in one embodiment. The first barb 244 can be about 5.99 in diameter.

In some embodiments, the height of the engagement feature 240 (e.g., the barbs 244 or 248) can be important. Barb height can be measured on the distance from a location of the barb that is farthest radially from an axis of the lumen through the connector 200 to the surface 220 adjacent to the barb 244, 248. In one embodiment, this distance is between about 0.005 inches and about 0.020 inches. In one embodiment, the height of the engagement feature is about 0.013 inches. In one embodiment, the height of the engagement feature is about 0.012 inches. In one embodiment, the height of the engagement feature or barb is between about 0.008 inches and about 0.009 inches. In one embodiment, the height of a first barb of the engagement feature 240 is about 0.012 inches and the height of a second barb of the engagement feature 240 is about 0.008 inches. The height and diameter of the engagement features 240 can be increased to increase retention force. In some embodiments, increasing these dimensions may be limited by the force required to advance the connector 200 into the catheter 100, which is generally done manually.

Another aspect of the engagement feature 240 is the length thereof or of individual portions thereof. For example, one embodiment has two barbs as discussed above. In one arrangement a distal-most barb is about 0.065 inches in length, though longer barbs could be used. In one embodiment, a proximal-most barb is about 0.065 inches in length. The proximal-most barb can be shorter or longer. For example, in one embodiment, the proximal-most barb is about 0.040 inches in length. In one embodiment, the distal-most barb is 0.065 inches and the proximal most barb is 0.040 inches.

Two additional features that contribute to the connection in some embodiments are the spacing between the barbs 244, 248 and the distance that the catheter is advanced past the proximal most barb.

Figure 5:
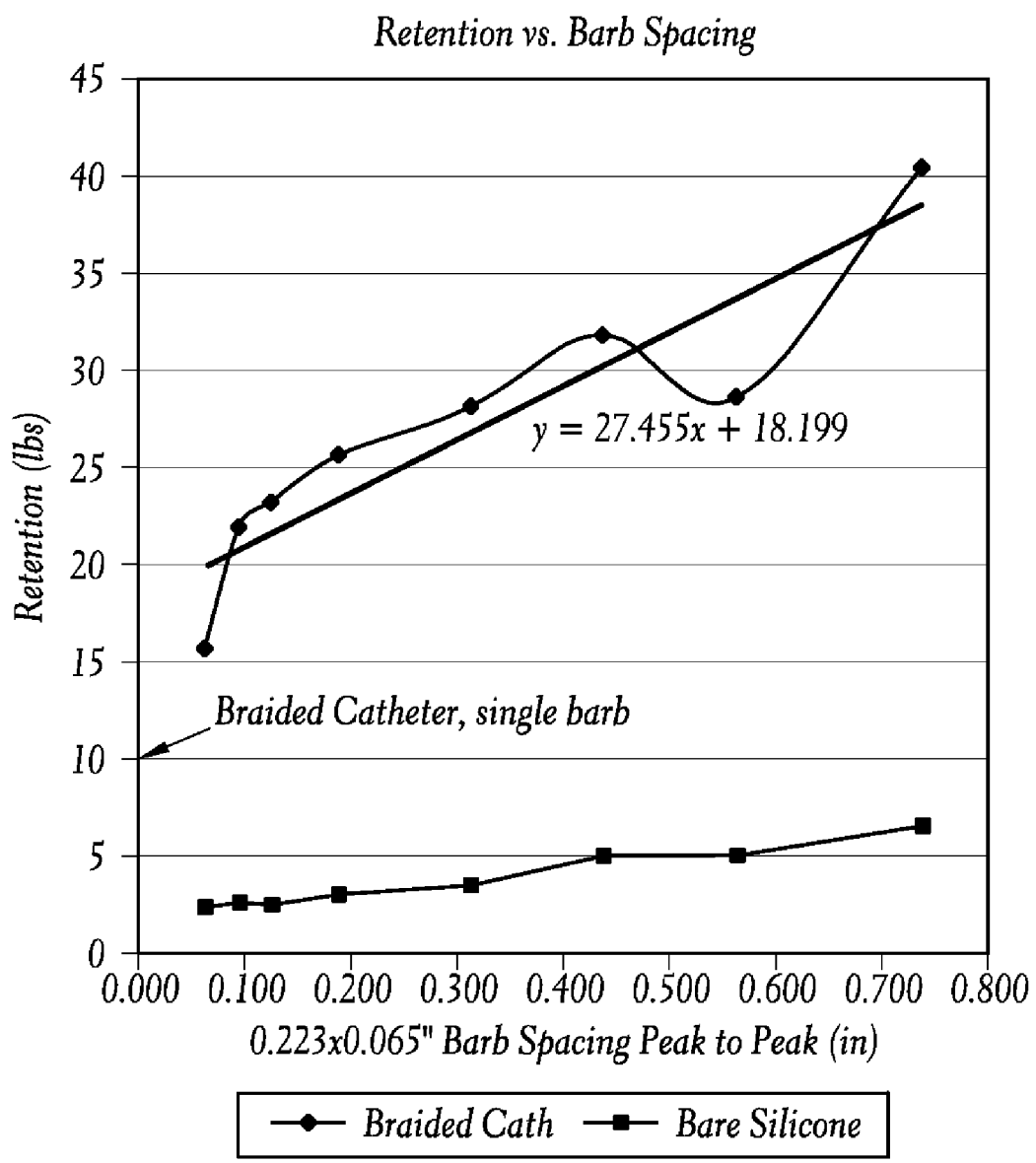
FIG. 5 is a graph illustrating a retention force for various engagement mechanisms described herein.

FIG. 5 demonstrates performance of various barb spacings. One configuration was tested with a maximum peak to peak barb spacing of about 0.740 inches. This chart shows a general trend of increase in retention force for greater barb spacing. Some of the increase in force observed in the chart could be attributable to a greater length of catheter in contact with the connector apparatus. As the barb spacing increased, so did the total length of connected catheter. FIG. 5 can be interpreted to indicate a minimum spacing of approximately 0.100 inches in some embodiments. At lesser barb spacings than this value the retention force drops rapidly. However, at increased spacings greater that this value, the force increases more slowly. In FIG. 5, one technique computed the rates of change as about 7 lbs/0.040 inches before an inflection point and about 1.2 lbs/0.040 inches after the critical point. This analysis employed a simple linear fit. One skilled in the art will recognize that a more complex fit of the data would produce a different mathematical description of the data. However, it is expected that other such curve fits would still reveal a relatively steep slope toward 0.100 inches and a flatter slope toward the middle of the data. Similarly in FIG. 6, discussed below, a more complex curve fit might reveal a generally asymptotic profile at one or both ends of the data set.

FIG. 5 shows that the dual barb configuration has superior connection strength to a single barb at all barb spacings and more than twice the strength once the peak to peak spacing exceeds about 0.100 inches. Also, the difference between bare silicone and braid reinforced silicone is apparent in FIG. 5. Note that in addition to the superior performance at any barb spacing, the slope of the line is greater for a braided catheter. This may be due in part to an amplified retention force generated by the combination of the retention feature 240 and the braided structure 140 in the catheter 100 upon connection of the catheter to the connector 200. This highlights the superiority of the braided flexible catheter over alternative designs. More particularly, the braided structure has much greater retention strength for a given barb dimension compared to a non-braided catheter of identical material. Also, the braided structure has the ability to further increase the retention strength by the use of multiple barbs on the connector 200. Also, the use of the braided structure compared to other reinforcements facilitates the use of barbs and optimized barb geometry on the connector 200. Moreover, the use of a soft elongate body 112 in the catheter 100 allows the braided structure 140 to neck down behind the barb and thereby increase the retention strength.

Given the results illustrated in FIG. 5, the spacing can be any suitable spacing, but as discussed below preferably is at least about 0.100 inches in an arrangement with two barb, or more. In one embodiment, the spacing between the peaks of adjacent barbs 244, 248 is about 0.229 inches. In one embodiment, the spacing between the peaks is about 0.240 inches.

Although FIG. 5 illustrates the vast improvements that can be achieved with the embodiments described above, in some applications an engagement mechanism having less redundancy provides adequate retention force. For example, FIG. 5 shows one embodiment where an engagement mechanism with a single barb provides about 10 pounds of retention force. This amount of force is sufficient for some applications. Also, although FIG. 5 shows that bare silicone generally provides a much lower retention force for various dual barb arrangements a combination of bare silicon and a connector can be sufficient in some arrangements, such as if the silicone is clamped at an outside surface thereof.

Figure 6:
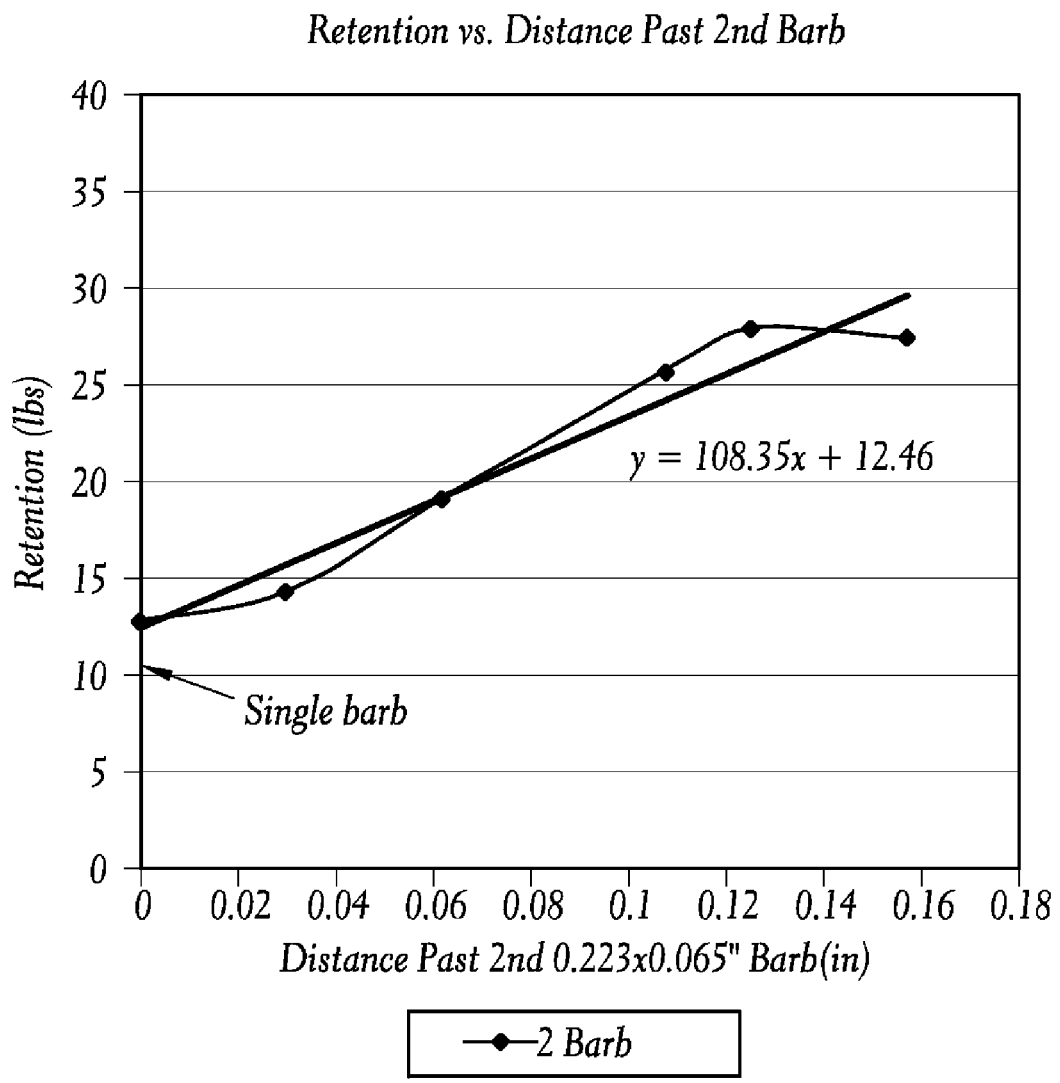
FIG. 6 is a graph illustrating a retention force corresponding to various techniques for connecting an engagement mechanism having two barbs.

In various embodiments, it is preferable to advance the catheter proximally past the proximal-most barb. The sensitivity to this variable is illustrated by FIG. 6. Also, a single barb example is illustrated in FIG. 6. The dual barb variable setup demonstrated little or no increase in retention force when the amount past the barb exceeded about 0.125 inches for one embodiment. This suggests that a suitable range for the catheter connection past the barb could be about 2-3 mm (0.080"-0.120") or about 1.5-4 mm (0.060"-0.160") for one embodiment of the catheter and connector combination.

FIG. 6 shows that a catheter flush with the proximal side of the second barb exceeds the retention strength of a single barb where the catheter is about 0.125 inch or less beyond the proximal side of the single barb. Other embodiments provide advancement beyond the retention feature 240 of between about 0.080 inches and 0.120 inches. In some embodiments, it is preferable to advance the catheter proximally past the proximal-most barb by between about 0.060 inches and 0.160 inches. In some embodiments, it is preferable to advance the catheter proximally past the proximal-most barb by about 0.010 or about 0.111 inches. In some embodiments, it is preferable to advance the catheter proximally past the proximal-most barb by between at least about 0.125 inches.

As discussed above, the engagement mechanism 32 particularly when configured to include portions of the catheter 100 and the connector 200 provides a number of clinical advantages over other arteriovenous shunt devices. Specifically, the combination of at least one of a braided structure and a barb in the engagement mechanism improves the ease of use of the device. As discussed above, the catheter 100 can be cut and connected without the need to further modify a catheter prior to connection. Also, the embodiments discussed herein have improved connectability in that a lesser force can be used to connect the engagement mechanism 32 than would be sufficient to disconnect the mechanism. Also, the system 10 is "one-size-fits-all" because it is configured to be trimmed to any desired length.

Other advantages that are provided include improved durability. The catheter 100 has many independent braided members 152 within the braided structure 140. The plurality of braided members 152 provides redundant support, which results in improved resistance to clamping and fatigue fracture. The plurality of braided members 152 also provides improvement in tensile strength. Compared to other prior approaches, less manufacturing steps are required, reducing the labor and cost of production. Also, it is expected that at least some of the embodiments of the catheter 100 withstand higher radial loads before collapsing and can be placed in a tighter radius without kinking than was possible with prior devices. In at least some applications, improved burst resistance (the ability to withstand high pressures without detaching from the connector or rupturing) can be advantageous but is not required.

Other advantages of the embodiments discussed herein include a benefit for the physician to receive feedback indicating that the catheter has been properly connected. For example, the multiple barb system provides increase in strength even when the catheter is minimally past a second barb. Visible deformation, e.g., by expansion of the catheter 100 or the braided structure 140, serves as a visual indication of proper attachment. This allows the user to observe the visible reference to insure that the catheter is past both barbs by referencing the two visible rings as the braided catheter goes over the first and second barbs. If not visible, this expansion can create ribbed portion on the otherwise smooth outer surface of the catheter 100 to provide a tactile confirmation of proper attachment.

Although it is recommended that the catheter be fully advanced against the central enlarged segment 250 of the connector 200, the integrity of the connection provides sufficient strength if inserted less than this amount, e.g., by only one-half of the distance from the barb 248 to the segment 250. This is expected to result in strength that is almost double when compared to a similar single barb system. When fully inserted it is expected that the strength will be almost tripled.

As discussed above, multiple and single barb engagement features can be suitable for secure connections. A properly designed single barb and braided catheter connection system can be made very secure, e.g., with about six times the retention force as a catheter made from the same material but without the braid. The second barb is expected to add at least a 100% increase in retention strength. This makes the engagement mechanism more robust, providing the added benefit of reducing the urgency of optimal insertion of the catheter over the connector to the enlarged section 250.

These features provide the desired level of security while providing the end user with both an increase in the confidence of achieving a secure connection.

What is claimed is:

1. A catheter for insertion into a blood vessel at a vessel insertion site for delivering blood after dialysis to a location downstream of the vessel insertion site, the catheter comprising:
   an elongate body having a proximal portion, a distal portion, and a lumen extending therebetween along a longitudinal axis,
   the elongate body being flexible and having an inner surface surrounding the lumen and an outer surface surrounding the inner surface; and
   a braided structure having a proximal end and a distal end, the braided structure being embedded within the elongate body such that the outer surface of the elongate body completely surrounds the braided structure,
   the braided structure extending from the proximal portion of the elongate body toward the distal portion thereof;
   wherein the proximal portion of the elongate body and the braided structure are configured to respond to an axial force by expanding such that the lumen is enlarged along the longitudinal axis for advancement over an engagement feature and for coupling with another blood conduit, the proximal portion of the elongate body and the braided structure also are configured to provide an enhanced connection of the elongate body to the engagement feature by applying a compressive force to the engagement feature when the proximal portion and the braided structure are placed over the engagement feature.

2. The catheter of claim 1, wherein the braided structure is configured to minimize compression and kinking of the elongate body and to enhance securement of the catheter to the engagement feature.

3. The catheter of claim 1, wherein the braided structure has a plurality of braid members that are woven together, each of said braid members having a cross-section with a first transverse dimension being greater than a second transverse dimension, the first transverse dimension being perpendicular to the second transverse dimension, the second transverse dimension being generally radially extending to minimize the crossing profile of the catheter.

4. The catheter of claim 3, wherein each braided member comprises two or more wires, each wire having a round cross-section.

5. The catheter of claim of claim 3, wherein the braided structure comprises a diamond pattern full load.

6. The catheter of claim 1, wherein the proximal end portion of the elongate body has a sizing region wherein the elongate body and the braided structure are adapted to be cut such that the catheter can be sized in-situ prior to being advanced over the engagement feature.

7. The catheter of claim 1, wherein the braided structure is adapted to maintain the lumen opens when the catheter traverses a bend radius of 1.0 inches or more.

8. The catheter of claim 1, wherein the braided structure is adapted to maintain the lumen opens when the catheter traverses a bend radius of 0.25 inches or more.

9. The catheter of claim 1, wherein the elongate body comprises a flexible elastomer and the braided structure comprises a shape memory material.

10. The catheter of claim 1, wherein the elongate body extends from the inner surface through apertures in the braided structure to the outer surface located radially outside of the braided structure, whereby the elongate body extends continuously from the inner surface to the outer surface through said apertures.

11. The catheter of claim 1, wherein the elongate body defines a single continuous extent of a single material from said inner surface to said outer surface through apertures of said braided structure.

12. The catheter of claim 1, wherein the outer surface of the elongate body comprises a smooth surface.

13. The catheter of claim 1, wherein the thickness from the inner surface to the outer surface is about 2 mm or less.

14. The catheter of claim 1, wherein the elongate body is configured to minimize delamination or other separation thereof from the braided structure.

15. The catheter of claim 1, wherein the braided structure defines a helix angle within a range of 40 degrees to 65 degrees.

16. The catheter of claim 1, wherein the braided structure defines a pic count within a range of 22 to 24.

17. The catheter of claim 1, further comprising a radiopaque marker located adjacent a distal end of the elongate body.

18. A system for connecting components of an implantable extravascular blood conduit having a proximal end adapted to couple with a first vascular segment and a distal end adapted to be inserted into a second vascular segment, the system comprising:
a catheter having a proximal portion and a distal portion configured such that, when implanted, the distal portion can freely float within the second vascular segment, the proximal portion comprising:
an elongate body defining an inner wall defining a blood flow lumen, the inner wall having an inner perimeter; and
a braided structure embedded in the catheter body and disposed about said lumen;
a connector for fluidly coupling the proximal end of the blood conduit with the catheter, the connector comprising:
a connector body having an outer surface defining a first outer perimeter and an inner surface defining a lumen; and
an engagement feature disposed on an outer surface of the connector body adjacent a distal end thereof, the engagement feature defining a second outer perimeter greater than the first outer perimeter;
the proximal portion of the catheter having a first configuration in the free state wherein the inner perimeter is less than the first outer perimeter and a second configuration when subject to an axial compression force wherein the braided structure expands to permit the inner perimeter of the catheter body to expand such that the proximal end portion of the catheter can be advanced over the engagement feature of the connector body, and wherein after release of the axial compression force, a retention configuration is provided in which the braided structure has a reduced diameter and exerts a retention force on the connector body, the retention force exceeding the axial compression force.

19. The system of claim 18, wherein a first compression force is required to connect the proximal end portion of the catheter to the connector over the engagement feature, and wherein a second force is required to disconnect the catheter from the engagement feature of the connector, the second force being greater in magnitude than the first force.

20. The system of claim 18, wherein the engagement feature comprises a plurality of barbs.

21. The system of claim 18, wherein the engagement feature comprises two barbs.

22. The system of claim 18, wherein the engagement feature comprises a region of increased perimeter spaced from a distal end of the connector.

23. The system of claim 22, wherein each of the barbs comprises a barb height of at least about 0.012 inches and wherein the separation between the two barbs is at least about 0.1 inches.

24. The system of claim 18, wherein the catheter body comprises a first blood flow conduit comprising a first material configured to minimize trauma to the second vascular segment and further comprising a second blood flow conduit formed of a material configured to be connected via anastomosis with the first vascular segment.

25. The system of claim 24, wherein the first material is one with high elasticity and low strength to minimize a force required for advancement of the catheter relative to the connector.

26. The system of claim 18, wherein the second outer perimeter is between about 8 and 28 percent larger than the inner perimeter of the blood flow lumen within the catheter body.

27. The system of claim 18, wherein the braided structure extends substantially continuously from the proximal end of the catheter distally within the proximal end portion such that the catheter can be trimmed to any suitable length and still be positionable in the first and second configurations.

28. The system of claim 18, wherein at least 10 lbs of force is required to disconnect the proximal end portion from the connector body.

29. The system of claim 18, wherein no more than about 8 lbs of force is required to connect the proximal end portion to the connector body.

30. The system of claim 18, wherein the force to connect the proximal end portion to the connector body is about ¼ of or less than the force to disconnect the proximal end portion from the connector body.

31. The system of claim 18, wherein the braided structure expands when placed in compression and necks inwardly when placed in tension to increase the retention force at the connector.

* * * * *